United States Patent [19]
Akiba

[11] Patent Number: 6,117,070
[45] Date of Patent: *Sep. 12, 2000

[54] PLUG DEVICE FOR ENDOSCOPIC INSTRUMENT CHANNEL

[75] Inventor: Haruo Akiba, Omiya, Japan

[73] Assignee: Fuji Photo Optical Co., Ltd., Omiya, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/980,008

[22] Filed: Nov. 26, 1997

[30] Foreign Application Priority Data

| Nov. 28, 1996 | [JP] | Japan | 8-332716 |
| Dec. 10, 1996 | [JP] | Japan | 8-346700 |
| Jan. 10, 1997 | [JP] | Japan | 9-014512 |
| Jan. 11, 1997 | [JP] | Japan | 9-014626 |

[51] Int. Cl.[7] ........................................ A61B 1/00
[52] U.S. Cl. ............................................. 600/154
[58] Field of Search .................. 600/154, 159, 600/104; 604/167

[56] References Cited

U.S. PATENT DOCUMENTS

| 4,240,411 | 12/1980 | Hosono | 600/154 |
| 4,653,477 | 3/1987 | Akui et al. | 600/154 |
| 4,809,679 | 3/1989 | Shimonaka et al. | 600/154 |
| 4,920,953 | 5/1990 | McGown | 600/154 |
| 5,209,219 | 5/1993 | Hollobaugh | 600/154 |

*Primary Examiner*—John P. Leubecker
*Attorney, Agent, or Firm*—Oblon, Spivak, McClelland, Maier & Neustadt, P.C.

[57] ABSTRACT

A plug device for use in an entrance passage which is provided on a manipulating head of an endoscope to guide a treating instrument like forceps into an instrument channel of the endoscope. The plug device includes a metallic outer shell, and a pressure relief member formed of a resilient material and fitted in the outer shell member, the pressure relief member having: a valve portion including a slit which is normally closed and openable on insertion of a treating instrument into the entrance passage; a pressure relief chamber; and throttle portions including apertures of different size located on the inner and outer sides of the pressure relief chamber within the entrance passage to the instrument channel of the endoscope. An auxiliary or secondary pressure relief chamber is formed between the valve member and the pressure relief member.

3 Claims, 10 Drawing Sheets

PLUG DEVICE FOR ENDOSCOPIC INSTRUMENT CHANNEL

FIELD OF THE ART

This invention relates to a plug device to be fitted in an entrance passage to an instrument channel on an endoscope.

PRIOR ART

Generally, endoscopes are largely constituted by a manipulating head, an elongated insertion instrument which is extended forward from the manipulating head for introduction into a body cavity or the like, and a universal cable which connects the endoscope to a light source. The insertion instrument is provided with an illumination means and an endoscopic observation means in its distal end portion. The manipulating head is provided with an angling knob and fluid feed button to be manipulated by an operator at the time of insertion into a body cavity to control the direction of the insertion instrument (angling operation) or to control the feed of gaseous or liquid medium. Further, the universal cable contains at least a light guide and is disconnectibly connectable to a light source at its proximal end.

After introducing the insertion instrument into a body cavity, an intracavitary region of interest is examined under an illuminated state, permitting one to render a necessary treatment on a diseased portion, if any, by the use of an endoscopically inserting instrument. On such occasions, it becomes necessary to introduce various surgical or bioptic instruments into the body cavity, e.g., instruments such as forceps, high frequency instruments, catheters etc., for instance, for removal of diseased portions, for coagulative treatments on bleeding spots or for medicinal or anaesthetic injections, or for the purpose of sampling tissues from intracavitary walls.

In many cases, endoscopes are internally provided with an instrument channel or channels in order to permit insertion of a surgical or bioptic instrument as mentioned above. The instrument channel of this sort is extended to an exit opening which is provided at the distal end of the endoscope in the proximity of endoscopic observation and illumination means. The proximal end of the instrument channel is extended into the manipulating head of the endoscope and connected to an inlet or entrance opening which is provided on the manipulating head.

In case an intracavitary region of interest is filled with body fluids or the like, an endoscopic examination is infeasible unless the body fluid is removed beforehand. To comply with such a requirement, it is desirable for the endoscope to contain a passage in its insertion instrument for sucking out body fluids or other fluidal contaminants. However, the endoscopic insertion instrument is normally required to be as small as possible in diameter for the purpose of facilitating passage through constricted tract or duct portions at the time of insertion into a body cavity and at the same time for lessening pains on the part of the patient. Therefore, it is the general practice to use an instrument channel on an endoscope as a suction passage. Normally, within a casing of the manipulating head assembly, a suction passage of this sort is branched off from the endoscopic instrument channel in its proximal end portion and led into a universal cable and coupled with a connector which is provided at the fore end of the universal cable. At the time of a sucking operation, the suction passage and the instrument channel of the endoscope are vacuumed by operation of a suction pipe which is detachably connected to the suction passage. For this purpose, a suction button is provided on the manipulating head thereby to turn on and off the communication between the suction pump and the endoscopic instrument channel, permitting to suck contaminant fluids out of a body cavity whenever necessary. It follows that the instrument channel on the endoscope, which provides a passage way for therapeutic or bioptic instruments, needs to be maintained in a hermetically sealed state during the vacuuming operation by the use of a plug device which is fitted in an entrance opening at the proximal end of the instrument channel.

Generally, a plug device of this sort is provided with a valve member within a casing to be fitted in the entrance opening on the manipulating head of the endoscope, the valve member being normally held in a closed state to seal the passage to the instrument channel except for those times when a therapeutic or bioptic instrument is inserted into or extracted from the instrument channel. Besides, in addition to the ability of maintaining a hermetical seal, the valve member is required to function as a check valve which would not open even when the instrument channel in conversely in a pressurized state. In order to meet these requirements, there has been known and used a valve member of slit construction, having a slit in a concave center portion of a partition wall of resilient material and of a predetermined thickness, in such a way that the slit is opened upon inserting a therapeutical or bioptic instrument into the caved-in center portion. This valve member has the concave center portion protruded into the fitting ring in such a way that the opposing edges of the slit are closed to maintain a sealed state unless acted on by an external force. The seal becomes even stronger in case the internal pressure of the instrument channel is elevated because the internal pressure tends to push the concave partition wall outward, holding the opposing edges of the slit into more tight and intimate contact with each other.

At the time of inserting a treating instrument into the instrument channel on the endoscope, a distal end portion of the instrument is pushed into the concave partition wall. Therefore, at the time of insertion, the concave partition wall acts as an access guide and, once the distal end of the instrument is pushed in, the opposing edges of the slit are forcibly opened apart. As a consequence, the treating instrument can be smoothly introduced into the endoscopic instrument channel past the valve member. In this regard, in an attempt to prevent air leaks through a valve member of this sort in a more reliable manner, Japanese Laid-Open Patent Specification H3-73127 discloses a plug device of dual valve construction having, in addition to a first valve member directly fitted in a plug case, a second valve member which is fitted in the first valve member. In this case, both of the first and second valve members are slit valves having a slit in a concave portion of a resilient partition wall.

No matter whether the valve member is of a single or dual valve construction, the opening and closing of the passage way to the endoscopic instrument channel is controlled by a slit. However, it is often the case that the slit is opened upon insertion of a treating instrument, and the opposing edges of the slit are set apart by an opened gap space. The width of the opened gap space varies depending upon the outside diameter of the endoscopically inserting instrument. Namely, in case the endoscopically inserting treating instrument is of a large outside diameter, the slit is opened wide, opening a broader gap space between the opposing edges of the slit and the circumferential surface of the inserted instrument.

Body cavities are maintained at a higher pressure than atmospheric, so that, when the suction passage within the insertion instrument of the endoscope is in a hermetically shielded state, the higher pressure similarly prevails in the instrument channel of the endoscope. However, when a treating instrument of a large outside diameter is inserted into the entrance to the instrument channel, a gap space is opened at the slit portion of the valve member as explained above, bringing the interior of the entrance housing into communication with the atmosphere. As a result, a pressure difference occurs between the entrance passage and the instrument channel. The instrument channel may have been used as a suction passage, and there may still remain body fluids or other liquids which might contaminate a treating instrument. If there are, there arises a problem because contaminants fluids will be pushed into the entrance passage due to the pressure difference between the instrument channel and the entrance passage. Besides, in some cases, for the purpose of securing a broad view field for endoscopic observation, a body cavity under observation is inflated with air by sending pressurized air through an air/water feed passage or the like. In such a case, the pressure difference becomes greater by elevation of the pressure on the side of the instrument channel, increasing the possibilities of contaminant fluids being pushed not only from the instrument channel into the entrance passage but also from its exit opening at the distal end of the endoscope into the instrument channel.

The valve member of dual valve construction, disclosed in the above-mentioned Japanese Laid-Open Patent Specification H3-73127, can maintain a strong hermetical seal as long as no treating instrument is inserted in the instrument channel. However, both of the two valve members in the dual valve construction are slit valves, so that, when a thick treating instrument is inserted, a gap space of a corresponding width is opened in each of the slits of the two valve members, resulting in drawing of contaminant fluids into the instrument channel from a body cavity and outflow of the drawn-in contaminant fluids through the opened gap spaces in the valve members. There is little possibility of the operators directly touching contaminant fluids of this sort because they normally put on gloves. However, outflow of contaminant fluids is not desirable not only from the standpoint of hygiene of the manipulating head of the endoscope and surrounding examination equipments, but also in consideration of difficulties of manipulating control means on the manipulating head which become slippery when covered with a large amount of contaminant fluids.

SUMMARY OF THE INVENTION

In view of the situations described above, it is an object of the present invention to provide a plug means for endoscopic instrument channel, which can securely prevent outflow of contaminant fluids through an entrance passage of the endoscopic instrument channel.

It is another object of the present invention to provide a plug device of the sort as mentioned above, which can minimize the pressure difference between the endoscopic instrument channel and an entrance passage to the endoscopic instrument channel at the time of insertion of a treating instrument of large diameter, thereby preventing body fluids or other contaminant fluids from being drawn into an entrance passage of the endoscopic instrument channel even if once taken up from a body cavity.

It is still another object of the present invention to provide a plug device of the sort as mentioned above, which is simple in construction and yet capable of preventing outflow of contaminant body fluids through an entrance passage of the endoscopic instrument channel.

In accordance with the present invention, the above-stated objectives are achieved by a plug device for endoscopic instrument channel, which comprises an outer shell member to be fitted in an entrance passage to an endoscopic instrument channel; a valve member formed of a resilient material and having a valve portion adapted to normally close the entrance passage unless a treating instrument is inserted therein; and a pressure relief section provided within the length of the entrance passage, the pressure relief section including a pressure relief chamber and first and second throttle portions located on the outer and inner sides of the pressure relief chamber to form constricted portions in the entrance passage when a treating instrument is inserted therein.

Contaminant body fluids in the instrument channel are drawn into the entrance passage mainly because of the existence of a gap space or gap spaces which are opened in a valve portion upon insertion of a treating instrument like forceps. However, even if a relatively large gap space is opened in a valve portion, contaminant body fluids in the instrument channel of the endoscope will not be pushed out toward the entrance channel as long as there is little difference in pressure between the instrument channel and the entrance passage. The pressure relief section which is provided in the plug device of the present invention serves to reduce this pressure difference. When a treating instrument is inserted into the instrument channel, the pressure relief section is maintained at a pressure level intermediate an internal pressure prevailing at the distal end of the instrument channel and the atmospheric pressure. For this purpose, the pressure relief section is constituted by a pressure relief chamber defining a predetermined pressure relieving space within the entrance passage to the instrument channel, and throttle portions located on the inner and outer sides of the pressure relief chamber and adapted to form constrictions in the entrance passage of treating instrument. The pressure relief chamber and throttle portions may be provided at one or a plurality of positions within the instrument entrance passage.

In a preferred form of the present invention, the valve member is fixedly fitted on a metallic outer shell member of the plug device, which internally contains the pressure relief member. Alternatively, the valve member may be formed or assembled integrally with the pressure relief member. In any case, the throttle portions on the inner and outer sides of the pressure relief chamber should be able to constrict the passage area to a minimum and, preferably, should be able to shut the passage substantially in a closed state. However, the throttle portions should not be a hindrance to the passage of treating instruments. For this reason, the throttle portions are preferred to be in the form of a resilient wall with an aperture which can be spread into a larger diameter upon insertion of a treating instrument. However, considering the narrowness of a gap space which is opened in the valve portion by insertion of a treating instrument of small diameter, the objectives of the present invention can be substantially achieved as long as they can perform the pressure-reducing function at the time of insertion of a treating instrument of large diameter. Therefore, the throttle portions may be in the form of an aperture of a diameter which just fits on a treating instrument of maximum diameter without opening a gap space therearound. If desired, one of the throttle portion may be in the form of a slit which is formed in a resilient wall. However, a relatively wide gap space is opened in the slit of this sort upon insertion of a thick treating instrument, it is desirable to use a throttle portion of slit form not on the outer atmospheric side of the pressure relief chamber but on the inner side thereof. In such a case, the throttle portion of slit form can also be used as the valve member.

BRIEF DESCRIPTION OF THE DRAWINGS

The above and other objects, features and advantages of the present invention will become apparent from the following particular description, taken in conjunction with the accompanying drawings which shows preferred embodiments of the invention and in which.

DESCRIPTION OF PREFERRED EMBODIMENTS

Hereafter, the present invention is described more particularly by way of its preferred embodiments with reference to the accompanying drawings.

Figure 1:
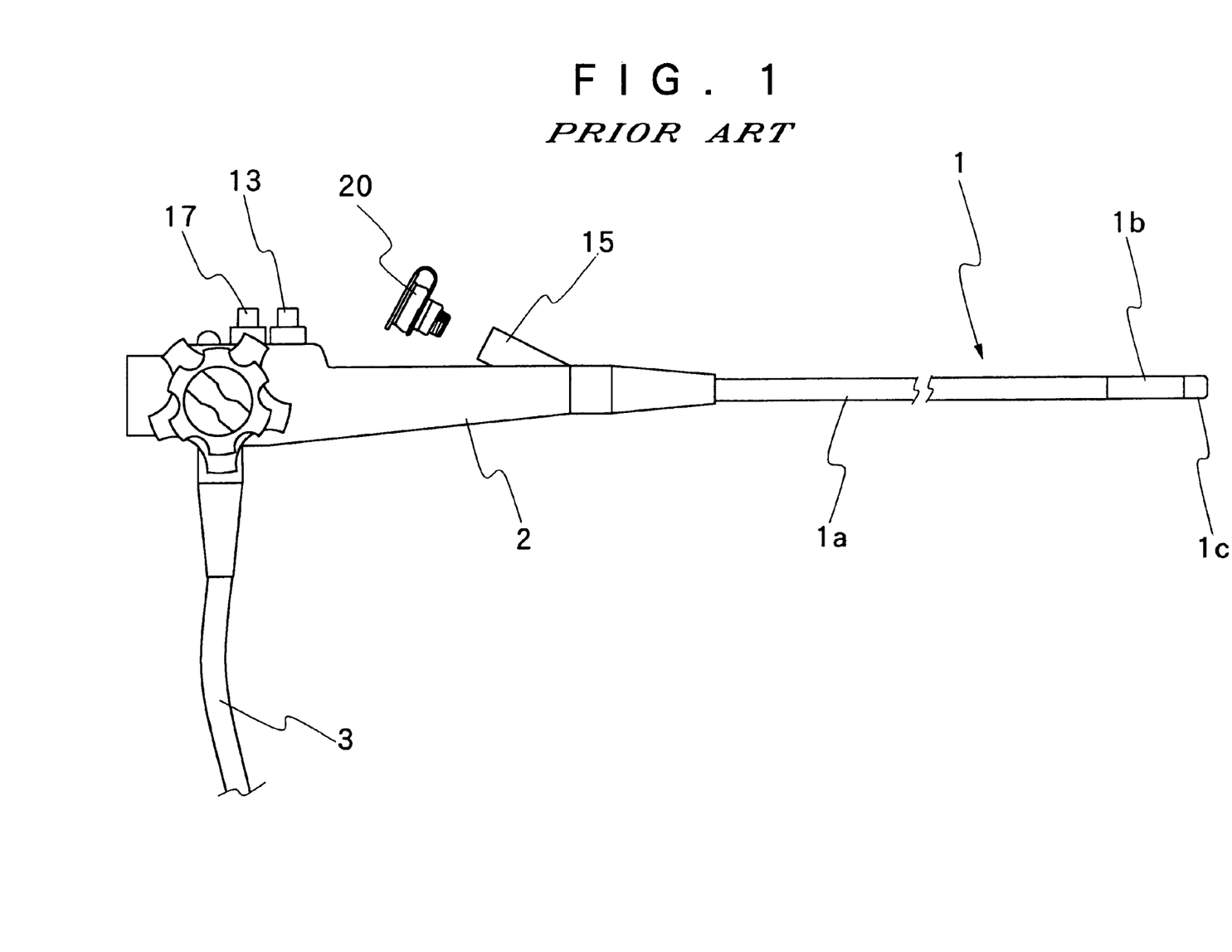
FIG. 1 is a partly cutaway schematic view of an endoscope.

Schematically shown in FIG. 1 is the general layout of an endoscope, which includes an elongated insertion instrument 1, a manipulating head 2 and a universal cable 3. In functional aspect, the insertion instrument 1, which is connected to and extended from the manipulating head 2, is composed of three sections. Firstly, the endoscopic insertion instrument 1 includes a flexible section 1a which forms the major part of the elongated insertion instrument 1 and which is flexibly bendable in arbitrary directions along a path of insertion. An angle section or joint 1b is connected to the fore end of the flexible section 1a, and further a rigid tip end section 1c is connected to the fore end of the angle section 1b.

Figure 2:
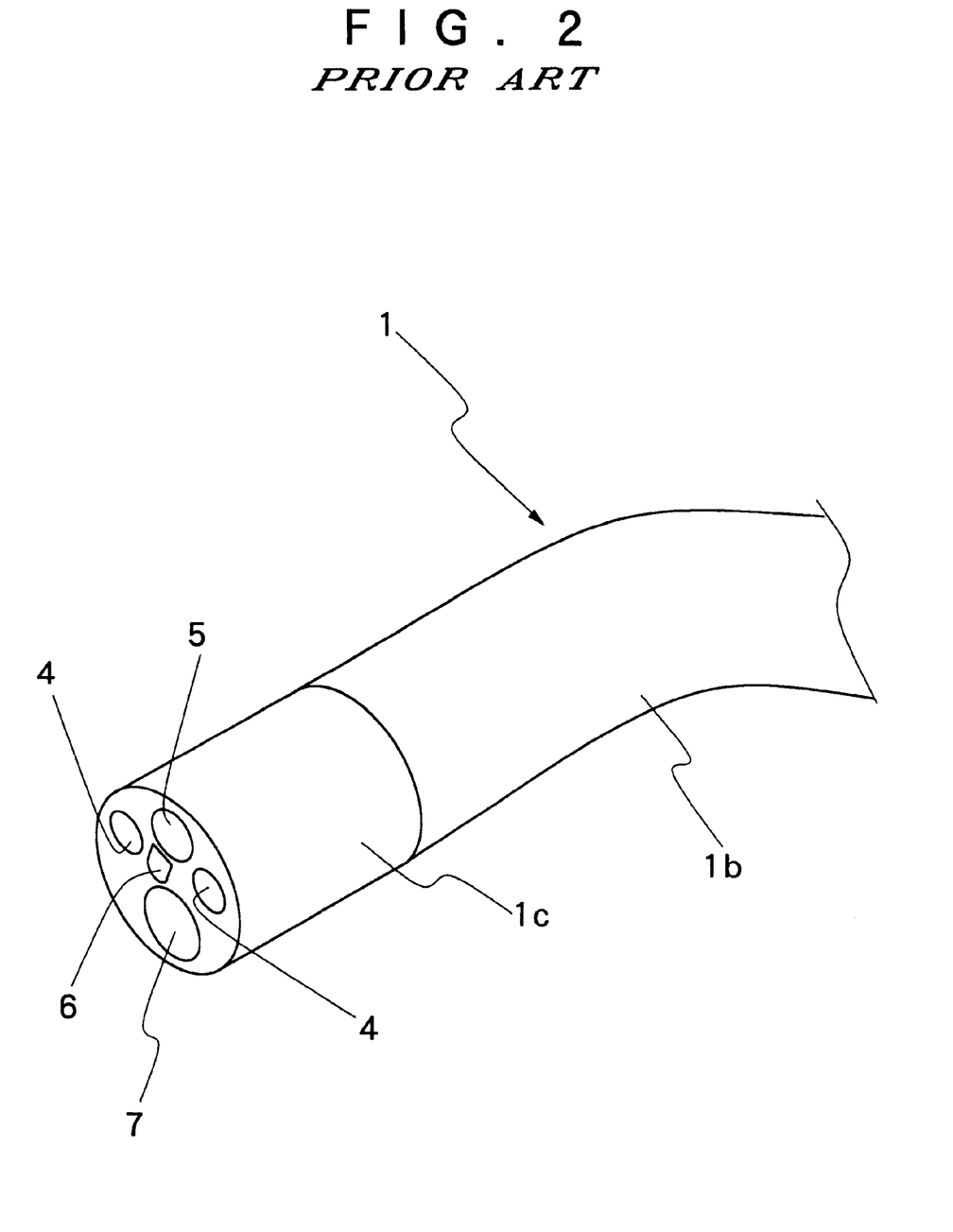
FIG. 2 is a schematic view of a fore end portion of an elongated insertion instrument of the endoscope.

As seen in FIG. 2, an illumination light emitting window 4 and an image pickup window 5 are provided on a distal end face (or at a lateral side of a distal end portion) of the rigid tip end section 1c. Located in the illumination window 4 is a light emitting end of a light guide, which is extended through the universal cable 3 and through the elongated insertion instrument 1 via the manipulating head 2. Accordingly, upon connecting the proximal end of the universal cable 3 to a light source, light rays are projected over broad areas of an intracavitary portion under observation through a diffusing lens which is fitted in the illumination window 4. On the other hand, an objective lens is fitted in the image pickup window 5 to form images of a body cavity on a solid-state image sensor or an image guide which is located at the focus of the objective lens.

Indicated at 6 is a nozzle which is opened toward the image pickup window 5 to spurt a cleaning liquid and wash the same when such has been smudged with body fluids, and, after washing, to blow compressed air toward the observation window 5 for removing liquid droplets therefrom, if any. Further, denoted at 7 is an exit opening of an instrument channel, through which a treating instrument such as forceps or the like is extended into a body cavity to render a necessary treatment, for example, to remove a diseased intracavitary portion.

Figure 3:
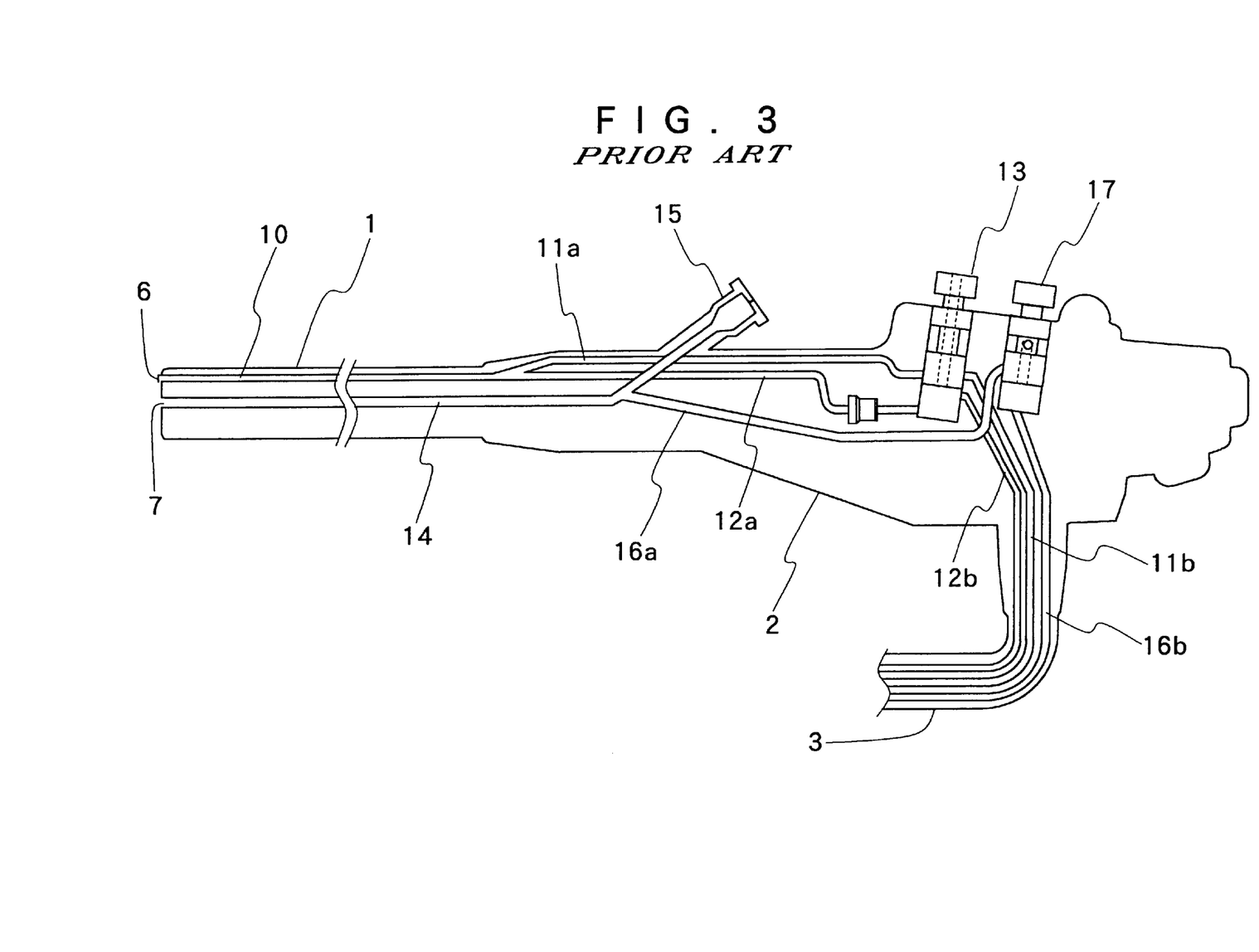
FIG. 3 is a partly cutaway schematic view of various passages which are provided internally of the endoscope.

FIG. 3 schematically shows various passages which are provided internally of the endoscope. Firstly, indicated at 6 is a fluid passage which is connected to the above-described nozzle 6. This fluid passage 10 is an air and water feed passage with which an air feed passage 11a and a water feed passage 12a are joined in a fore end portion of the insertion instrument 1. On the manipulating head 2, the air feed passage 11a and the water feed passage 12a are connected to an air/water feed valve 13, which is connected to air and water sources through an air supply passage 11b and a water supply passage 12b, respectively. Accordingly, air supply from the air supply passage 11b to the air feed passage 11a as well as water supply from the water supply passage 12b to the water feed passage 12a can be turned on and off by manipulating the air/water feed valve 13 with fingers.

Indicated at 14 is an instrument channel which is coextensively provided within the insertion instrument 1 of the endoscope. The fore end of the instrument channel 14 is connected to the above-mentioned exit opening 7, while the other or the proximal end is connected to an entrance passage 15 which is provided at the foot of the manipulating head 2. Further, the other end of the instrument channel 14 is connected to a suction passage 16a in the vicinity of its junction point with the instrument entrance passage 15. The other or proximal end of the suction passage 16a is connected to a suction valve 17, which is in turn connected to a suction passage 16b from a vacuum source of syphondrainage. Thus, the communication between the suction passages 16a and 16b is turned on and off by operating the suction valve 17 accordingly.

As shown also in FIG. 1, the air/water feed valve 13 and suction valve 17 can be operated by way of manual control means which are provided on the manipulating head 2. The air supply passage 11b, water supply passage 12b and the suction passage 16b on the side of the vacuum source are led into the universal cable 3 and disconnectibly connected to known compressed air source, water supply source and vacuum source, respectively, through a connector which is provided at the proximal end of the universal cable 3 although not shown in the drawings.

The suction passage 16a is connected to the instrument channel 14, so that it is difficult to apply a suction force thereto as long as the entrance passage 15 is in communication with the atmosphere. The instrument entrance passage 15 therefore needs to be closed in a hermetically sealed state, and, for this purpose, a plug device 20 is fitted in the opening of the instrument entrance passage 15.

Figure 4:
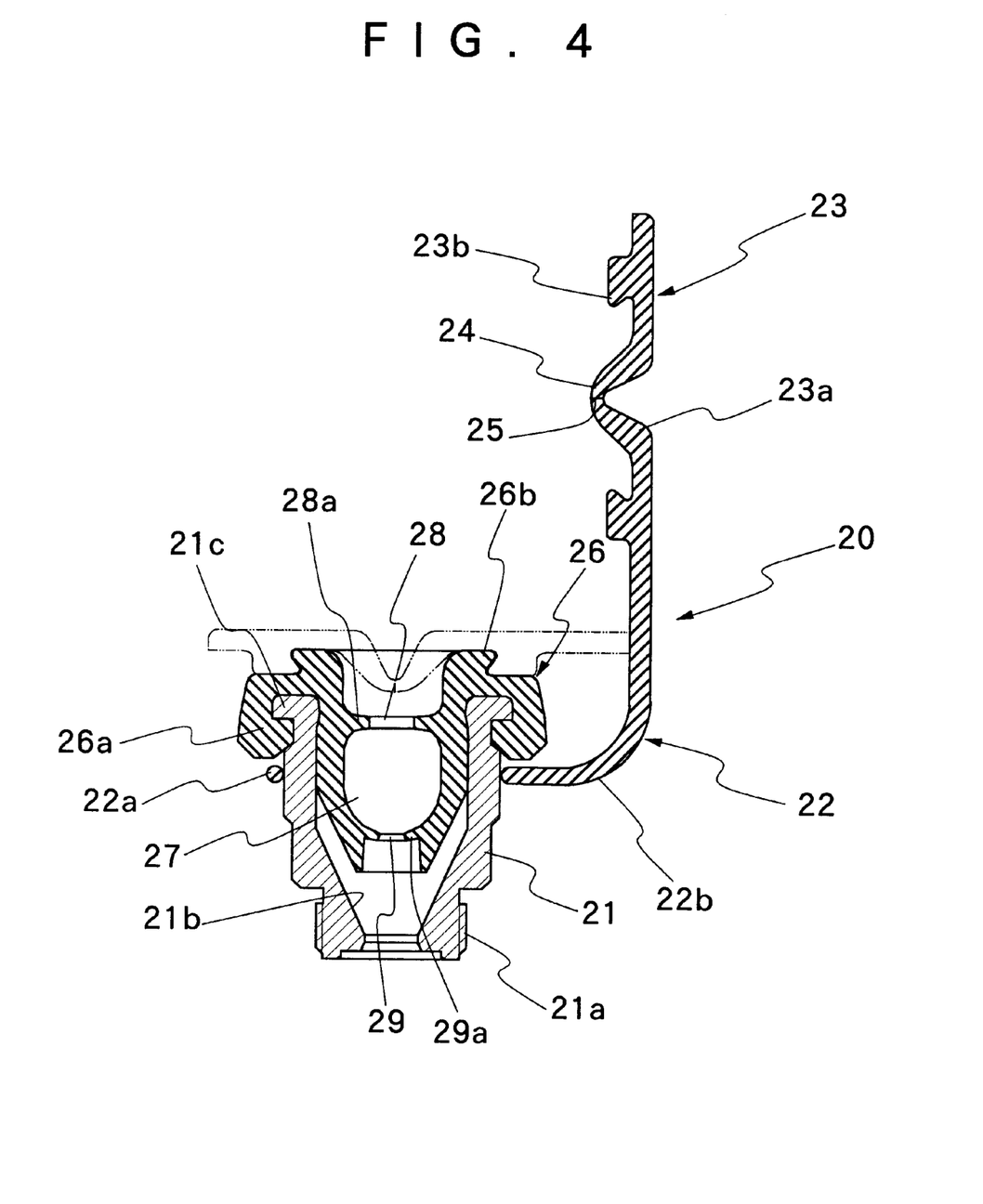
FIG. 4 is a schematic sectional view of a plug device according to a first embodiment of the present invention.

As shown particularly in FIG. 4, the plug device 20 includes an outer shell member 21 of rigid material such as hard synthetic resin, metal or the like. The outer shell 21 is provided with an external screw 21a on the outer periphery thereof for threaded engagement with an internal screw 15a on the inner periphery of the entrance passage 15. The outer shell member 21 is open at the opposite ends thereof, and provided with a tapered surface 21b on its inner periphery, converging forward toward its fore end to guide an inserted treating instrument smoothly toward the instrument channel. Thus, the inner tapered surface 21b of the outer shell member 21 forms a forwardly converging passage which however is broader than the maximum diameter of treating instrument even at its narrowest portion. Securely attached on the outer periphery of the outer shell member 21 is a connecting member 22 which is constituted by a ring portion 22a and a resilient strap portion 22b. Provided at the fore end of the connecting member 22 is a valve member 23, which is formed of a resilient material like rubber and integrally provided with a valve portion 23a and an anchor portion 23b.

The valve member 23 is provided with a concavely recessed wall 24 substantially centrally of its valve portion 23a, the bottom of the concavely recessed wall 24 being protruded on the same side as the anchor portion 23b. The concavely recessed wall 24 is provided with a slit 25 which can be opened and closed to serve as a valve means. The slit 25 can be spread open through elastic deformation upon pushing in a treating instrument, and has an enough length to permit passage of a treating instrument of maximum diameter. When the concavely recessed wall 24 is free of any external force, the opposing edges of the slit 25 are closed in intimate contact with each other to serve as a seal means. Besides, the slit 25 which is formed in the concavely recessed wall 24 functions as a check valve because it can be opened only in the inward direction and not in the outward direction. On the other hand, when a treating instrument is pushed into the concavely recessed wall 24, the slit 25 is forcibly spread open to permit passage of the treating instrument through the valve member 23. At this time, the concavely recessed wall 24 functions as an initial guide for access to the entrance passage.

The valve member 23 is not directly placed in the outer shell member 21. Instead, a pressure relief member 26 is removably fitted in the outer shell member 21, and, as indicated by imaginary line in FIG. 4, the valve member 23 is fitted in the pressure relief member 26. The pressure relief member 26 is formed of a resilient material like rubber, and provided with a holder rim portion 26a at its outer end contiguously around the outer periphery thereof. The holder rim 26a is securely fitted on a flange portion 21c, which is formed around the outer end of the outer shell member 21, in such a way as to embrace the latter. Provided on the outer side of the rim portion 26a is a stopper portion in the form of an annular lip 26b which is projected radially outward and which is engageable with the anchor portion 23b of the valve member 23 to stop the latter in position in a fixed state. When the valve member 23 is fitted on the pressure relief member 26, the concavely recessed wall 24 of the valve member 23 is protruded into the pressure relief member 26.

A passage is formed axially through and internally of the pressure relief member 26 for receiving a treating instrument. The pressure reducing member 26 contains a pressure relief means within its axial passage, which functions to reduce the pressure difference between the instrument channel 14 of the endoscope and the atmosphere. More specifically, a pressure relief chamber 27 is defined in the internal passage of the pressure relief member 26 between first and second throttle portions 28 and 29, which are located on the outer and inner sides of the pressure relief chamber 27, respectively. The pressure relief chamber 27 has a relatively broad space in contrast to the first and second throttle portions 28 and 29, which function to substantially block communication with the atmosphere of the instrument channel 14 of the endoscope or to constrict the flow passage area to the effect that the pressure relief chamber 27 is maintained at a pressure level intermediate between the internal pressure of the instrument channel 14 and the atmospheric pressure.

In the insertion passage through the pressure relief member 26, the first throttle portion 28, which is located on the outer side of the pressure relief chamber 27 or on the side of the valve member 23 is provided with an aperture corresponding in diameter to a treating instrument with a maximum diameter among various instruments to be endoscopically introduced into a body cavity through the instrument channel of the endoscope, more specifically, an aperture of a diameter same as or slightly greater or smaller than a treating instrument of maximum diameter. On the other hand, the second throttle portion 29, which is located on the inner side of the pressure relief chamber 27 or on the side of the instrument channel 14 of the endoscope, is provided with an aperture of a diameter substantially the same as or corresponding to a treating instrument of minimum diameter. Therefore, in most cases the second throttle portion 29 is forcibly pushed open when a treating instrument is passed therethrough. In order to insure smooth passage of treating instruments of various diameters, the second throttle member 29 is reduced in wall thickness in its perforated resilient wall portions 29a to such a degree that its aperture can be readily widened to a larger diameter upon insertion of a treating instrument of a larger diameter.

Further, the pressure relief member 26 is provided with a space of predetermined breadth between the locking lip portion 26b and radial wall 28a of the first throttle member 28 to receive the concave wall portion 24 of the valve member 23 when the latter is connected to the pressure relief member 26. This space forms an auxiliary and secondary pressure relief chamber with respect to pressure relief chamber 27 and which provides room for spreading movements of the slit 25 in the concave wall portion 24, which is opened upon insertion of a treating instrument.

Figure 5A:
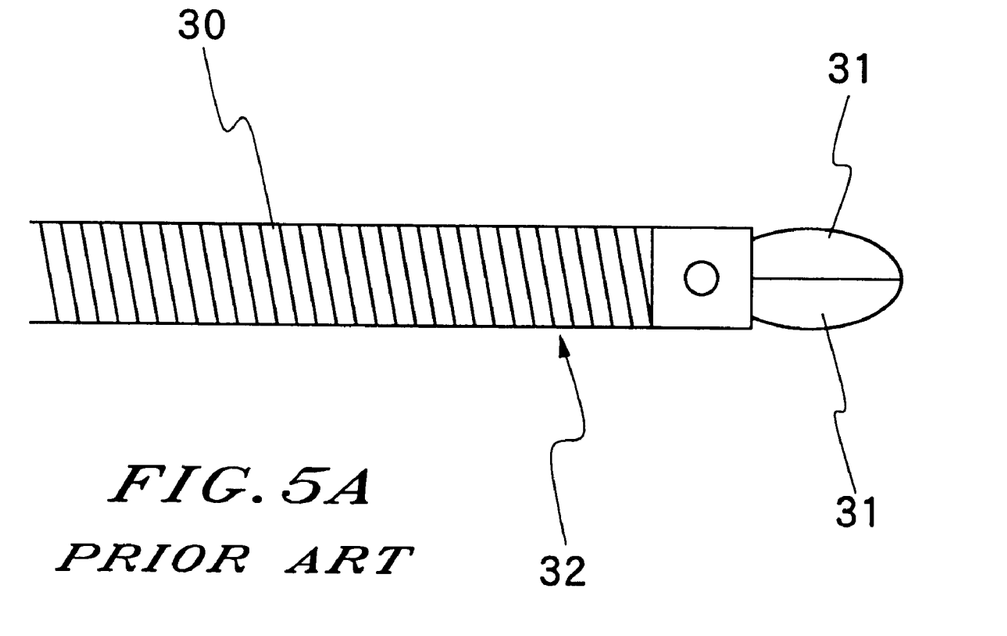
FIG. 5 is a schematic illustration of a treating instrument which is designed to be inserted into a body cavity by way of an instrument channel in the endoscope, showing at (a) forceps as an example of treating instrument of maximum diameter and at (b) a cannulation tube as an example of treating instrument of minimum diameter.
Figure 5B:
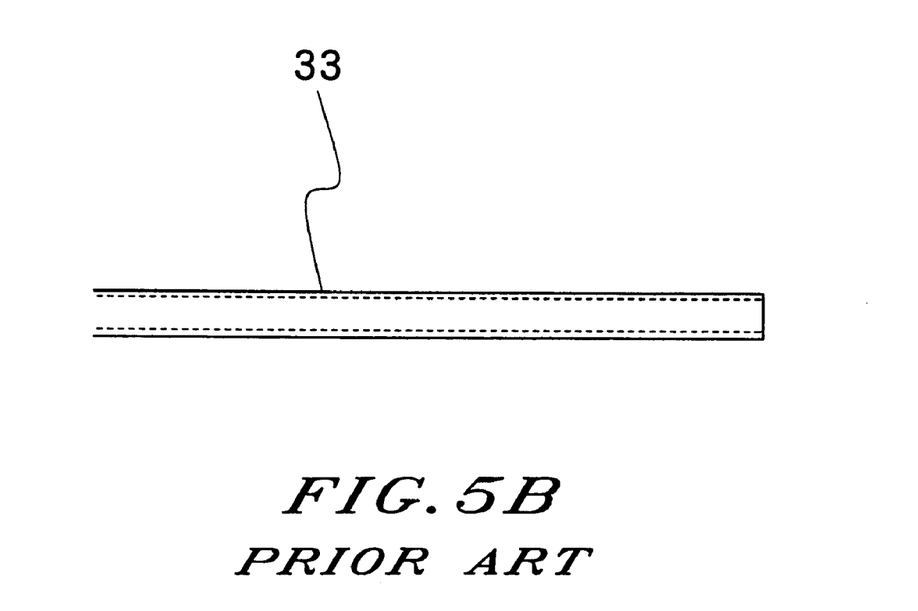

Among various treating instruments which are designed to be inserted into a body cavity through an endoscopic instrument channel 14, presumably an example of treating instrument with maximum diameter is forceps 32, which has a pair of openable pincer claws 31 at the fore end of a flexible coil tube 30 as shown at (a) of FIG. 5. The pincer claws 31 of the forceps 30 are opened and closed through a link mechanism which is not shown in the drawings. In order to remote-control opening and closing actions of the pincer claws 31, operating wires are passed internally of the flexible coil tube 30. On the other hand, an example of treating instrument with minimum diameter is a cannulation tube 33 which consists of a narrow tube of flexible synthetic resin material as shown at (b) of FIG. 5, and, for example, inserted into papilla for discharge of bile.

In use, the plug device 20 is set on the endoscope by threading the outer shell member 21 into the entrance passage 15 of the endoscope, after fitting the pressure relief member 26 and valve member 23 successively in the outer shell member 21. Then, a treating instrument is introduced into the instrument channel 14 through the plug device 20 until the fore end of the treating instrument is extended into a body cavity from the exit opening of the instrument channel 14 over a certain extension length which is required to render a necessary treatment. Since the pressure in the body cavity is higher than the atmospheric pressure, in some cases it becomes necessary to send pressurized air into the body cavity in order to secure a broad view field for the endoscopic examination. In such a case, the difference in pressure between the body cavity and the atmosphere becomes even greater. Therefore, when body fluids or other contaminants have been drawn out through the instrument channel 14 prior to an endoscopic examination, residues of such body fluids may still remain in the instrument channel 14 or may have deposited on fore end portions of the endoscopic insertion instrument. Under such circumstances, the residue of contaminant body fluids can be drawn to flow out through the entrance passage 15 due to difference in pressure between the instrument channel 14 and the entrance passage 15.

Figure 6A:
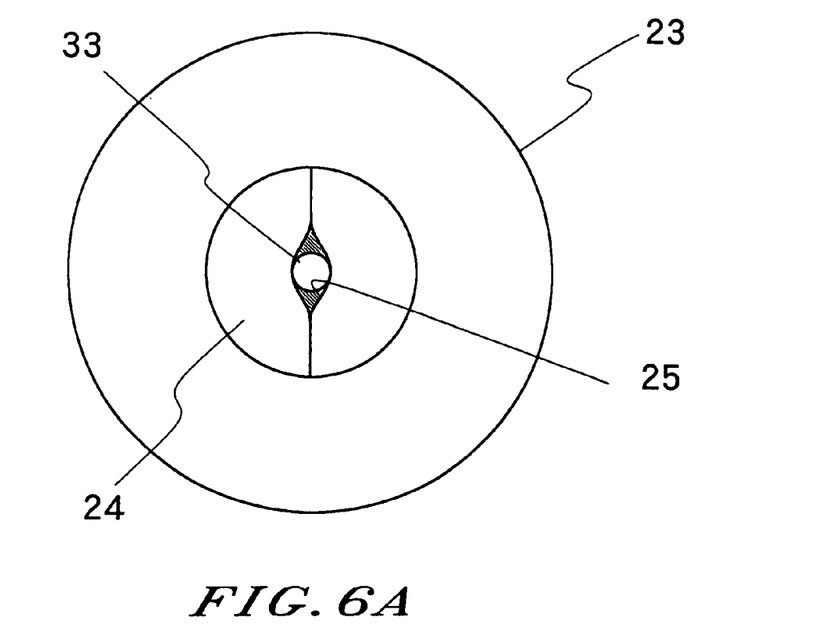
FIG. 6 is a diagrammatic illustration of gap spaces which are opened in a valve member by insertion of a treating instrument, showing at (a) a gap space which is opened by insertion of a cannulation tube and at (b) a gap space which is opened by insertion of forceps.
Figure 6B:
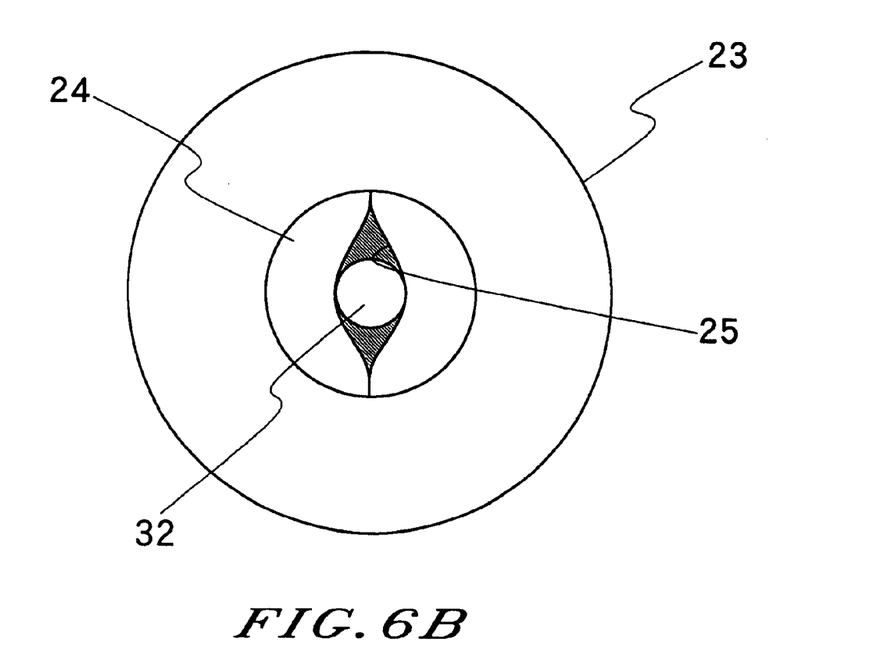

The slit 25, which is formed in the valve member 23 of the plug device 20 for valve action, is forcibly spread open as a treating instrument passes therethrough, opening a gap space between the circumference and the opposing edges of the slit 25. In case the treating instrument is a narrow one like the cannulation tube 33, the opened gap space is extremely small as indicated by hatching in FIG. 6(a). However, when the inserted treating instrument is as thick as forceps 32, a wider gap space is opened as indicated by hatching in FIG. 6(b), and it becomes difficult for the slit 25 to maintain a seal by its valve action.

Figure 7:
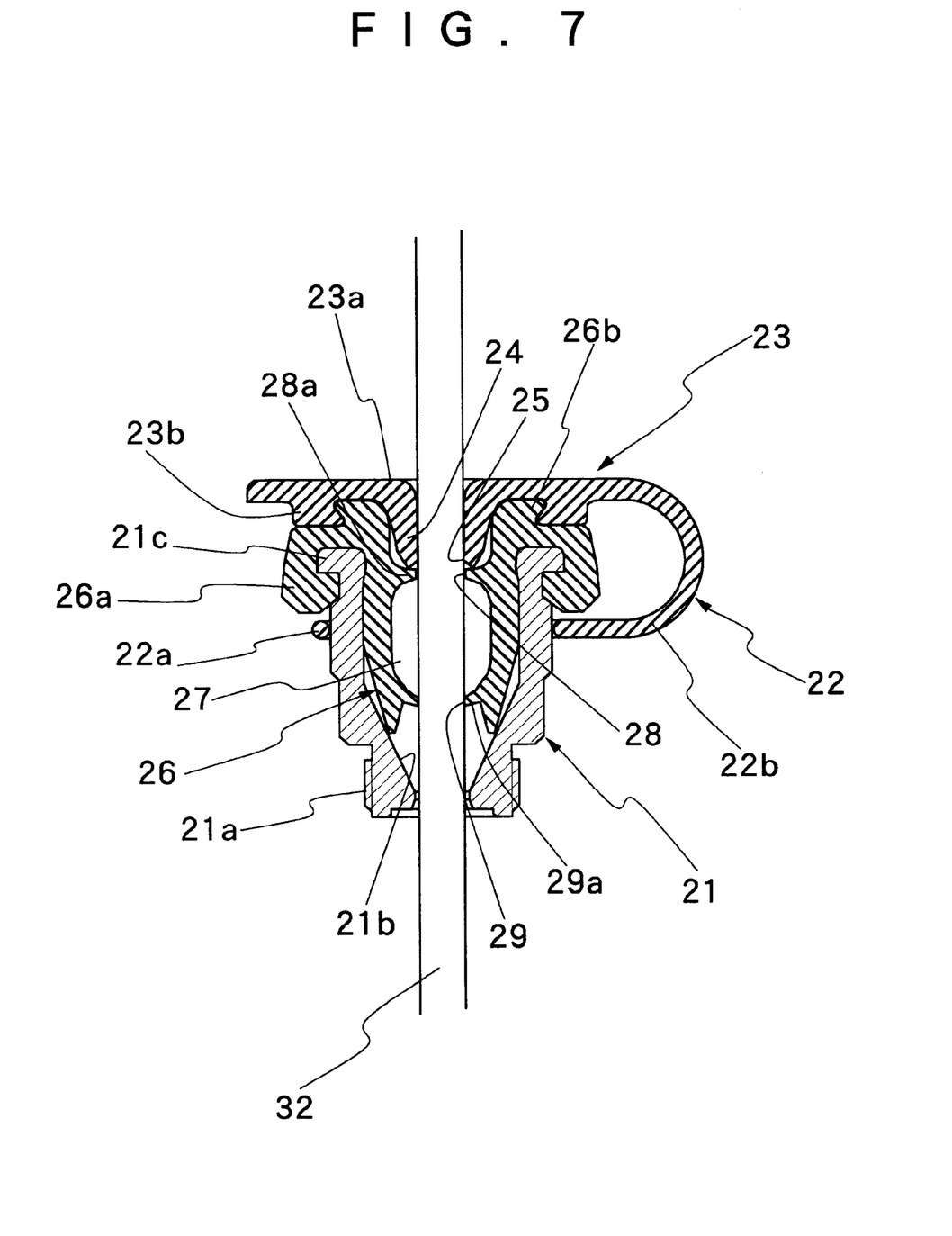
FIG. 7 is a schematic sectional view of the plug device receiving forceps of large diameter.

However, the plug device 20 is provided with the pressure relief member 26 in its internal passage thereby to block communication or to moderate the pressure difference between the exit side 7 and the entrance side of the instrument channel 14. Namely, as shown in FIG. 7, when forceps, typical of a thick treating instrument, is inserted into the pressure relief member 26, the aperture in the second throttle portion 29, which is smaller than the outside diameter of the flexible coil tube 30 of the forceps 32, is spread to a larger diameter, with resilient wall portions 29a of the second throttle member 29 in intimate contact with the circumference of the flexible coil tube 30. Accordingly, at this position, the instrument channel 14 is shielded from the atmosphere.

However, a perfect seal cannot be expected at this position because the resilient wall portion 29a is thinned down for the purpose of facilitating the passage of the treating instrument through the second throttle member 29. Besides, it is probable that the aperture of the second throttle member 29 is widened due to deformation of the thin resilient wall portion 29a which is repeatedly spread by insertion of various treating instruments. In that case, it may become difficult for the resilient wall portion 29a to form a tight seal even around a treating instrument of large diameter. Namely, it becomes difficult to maintain a perfect seal by the second throttle member 29 alone.

Nevertheless or even if the seal by the second throttle member 29 is imperfect, it at least constricts the flow passage area to a minimum by narrowing the gap space around the circumference of the inserted treating instrument. Provided on the outer side of the second throttle member 29 is the pressure relief chamber 27, which has a relatively broad space, along with the first throttle member 28 as described above. Therefore, upon insertion of a treating instrument, the flow passage is constricted on the inner and outer sides of the pressure relief chamber 27 by constrictive actions of the first and second throttle members 28 and 29. As a consequence, even if there is a pressure difference between the instrument channel 14 and the atmosphere, the pressure relief chamber 27 is maintained at an intermediate pressure level. Therefore, the pressure difference of the instrument channel 14 from the outer pressure relief chamber 27, which communicates with the instrument channel 14 through the second throttle member 29, is minimized as compared with the difference from the atmospheric pressure. This precludes outflow of body fluids or other contaminants from the instrument channel 14, which would otherwise be pushed out into the entrance passage 15 of the endoscope due to a large pressure difference. This plug arrangement will give rise to no problems in particular in inserting thick treating instruments, i.e., treating instruments thicker than the diameter of the aperture in the second throttle member 28, because thick instruments generally have greater stiffness. In case the aperture diameter of the first throttle member 28 is smaller than the maximum outside diameter of treating instruments, its throttling effects can be enhanced all the more and, when a treating instrument of maximum diameter is inserted, a seal can be formed around the inserted instrument substantially by the first throttle member 28 alone. Needless to say, it can produce sufficient throttling effects even after its aperture has been widened as a result of repeated insertion of treating instruments.

The first throttle member 28 can produce flow passage throttling effects in case of a treating instrument of large diameter like forceps 32, which has little difference in diameter from the aperture of the second throttle member 28 as mentioned hereinbefore. However, in case of a narrow treating instrument like the above-described cannulation tube 33, it becomes difficult to expect sufficient throttling effects at the position of the second throttle member 28 due a large difference in diameter. Instead, in the latter case, the slit 25 is opened only in a small degree on insertion of a narrow treating instrument, and can function as a first throttle member. In this instance, the pressure relief chamber 27 is extended to the outer side, namely, up to the valve member 23 through the first throttle member 28, and, in cooperation with the second throttle member 29, can produce the same pressure-relieving effects substantially to the same extent as in the case of thick treating instruments.

Thus, when a treating instrument is inserted into the plug device 20, the pressure relief chamber 27 is maintained at an intermediate pressure level between the internal pressure of the instrument channel 14 and the atmospheric pressure, by the throttle members which are provided on the inner and outer sides of the pressure relief chamber 27 to close the gap spaces around the circumference of the inserted treating instrument and, if unable to close the gap spaces completely, at least to throttle a fluid flow area in the entrance passage of the endoscopic instrument channel. Even if seals by the throttle members are incomplete, there is no possibility of residues of contaminant body fluids flowing out toward the instrument entrance passage 15. Especially, even when the aperture diameter of the second throttle member 29 has been widened to some extent as a result of repeated insertions of treating instruments, it still retains the throttling function to produce similar pressure relieving effects in cooperation with the pressure relief chamber 27.

Figure 8:
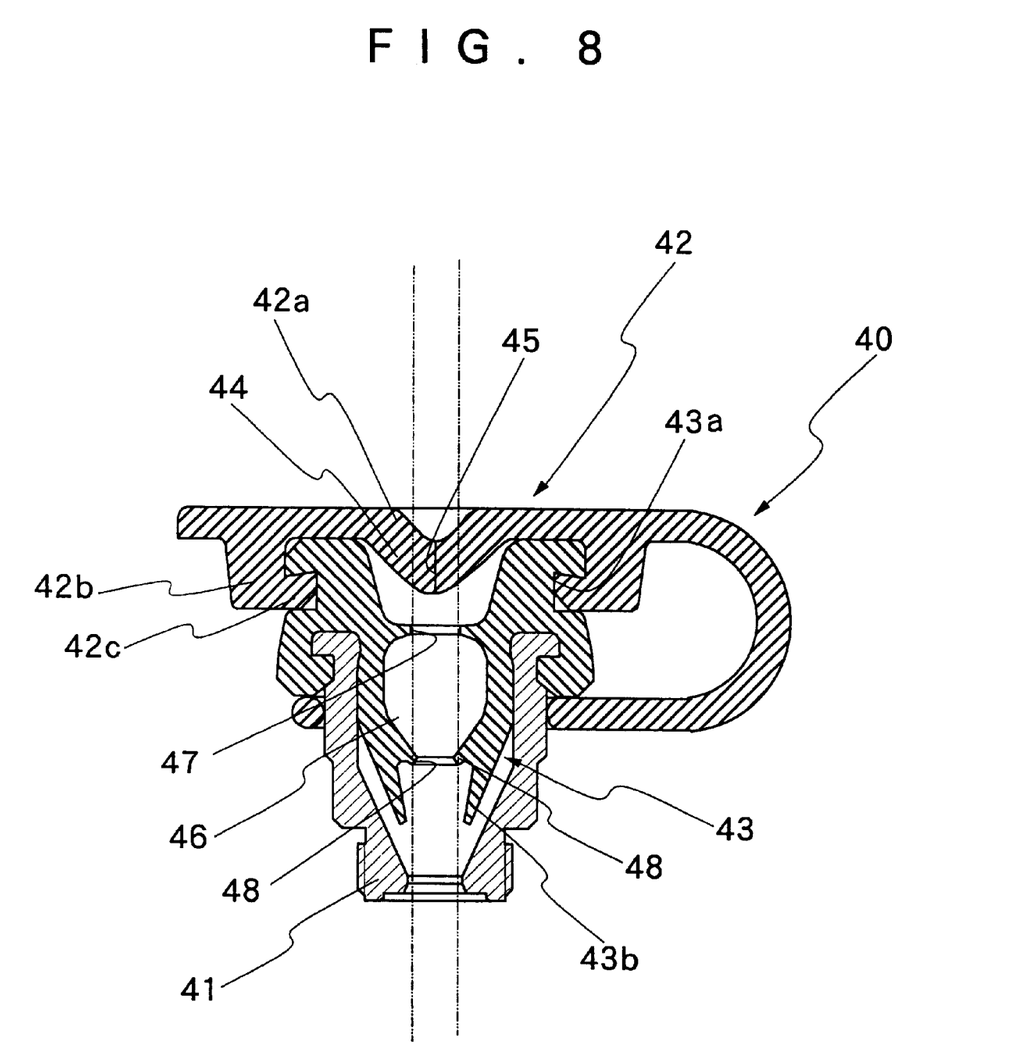
FIG. 8 is a schematic sectional view of a plug device according to a second embodiment of the present invention.

Referring now to FIG. 8, there is shown a second embodiment of the present invention, employing a plug device 40 which is similarly constituted by a valve member 42 and a pressure relief member 43. The pressure relief member 43 is fixed in an outer shell member 41 through the same fixation mechanism as explained hereinbefore in connection with the first embodiment. In this case, however, as a mechanism for locking a valve member 42 on the pressure relief member 43, an annular groove 43a is formed on and around the outer periphery of the pressure relief member 43, while a tubular rim 42b is provided around a valve portion 42a of a valve member 42, the tubular rim 42b having an annular protuberance 42c on the inner periphery thereof for interlocking engagement with the annular groove 43a on the part of the pressure relief member 43.

The valve member 42 is provided with a concavely recessed portion 44 containing a slit 45 for valve action. On the other hand, the pressure relief member 43 is provided with a pressure relief chamber 46 between first and second throttle portions 47 and 48. In this regard, the second embodiment is arranged in the same manner as the foregoing first embodiment. Of the two throttle portions, the second throttle portion 48 is provided with an aperture which is smaller than treating instruments of large diameter. Therefore, in order to permit passage of a thick treating instrument, the second throttle portion needs to be spread into a larger diameter. Although the second throttle portion of the pressure relief chamber is constituted by a thinned-down resilient wall in the foregoing first embodiment, the pressure relief chamber 46 of this embodiment has its inner peripheral wall gradually converged in the inward direction toward the second throttle portion 48, and provided with a skirt portion 43b of a larger diameter extending forward of the second throttle portion 48. Namely, in this case, the second throttle portion 48 of the pressure relief member 43 is defined by an annular protuberance or ridge 49 which is formed at the boundaries of the skirt portion 43b. Further, outer peripheral surfaces of the skirt portion 43b of the pressure relief member 43 are disposed at a predetermined space from inner peripheral surfaces of the outer shell member 41, so that, upon insertion of a treating instrument which is thicker than the aperture diameter of the second throttle portion 48, the skirt portion 43b is spread in radially outward directions through resilient deformation to widen the passage of the second throttle portion 48.

Even when the plug device is arranged as in the above-described second embodiment, it can provide the same pressure relieving function to reduce the pressure difference of the instrument channel, by means of the pressure relief chamber 46 of the pressure relief member 43, in cooperation with the first and second throttle portions 47 and 48 at the outer and inner boundaries of the pressure relief chamber 46, when a thick treating instrument is inserted into the instrument channel, and by means of the inner space of the pressure relief member 43 including the pressure relief chamber 46, in cooperation with the slit 45 and the second throttle portion 48 at the outer and inner boundaries of its inner pressure relieving space, when a thin treating instrument is inserted into the instrument channel. Besides, the second throttle portion 48 which is constituted by an annular protuberance in this case can guarantee higher durability, restoring its original state smoothly even after repeated expansions by insertion of thick treating instruments, namely, suppressing as much as possible the possibilities of the second throttle portion 48 flattening unrestorably in a widened state.

Figure 9:
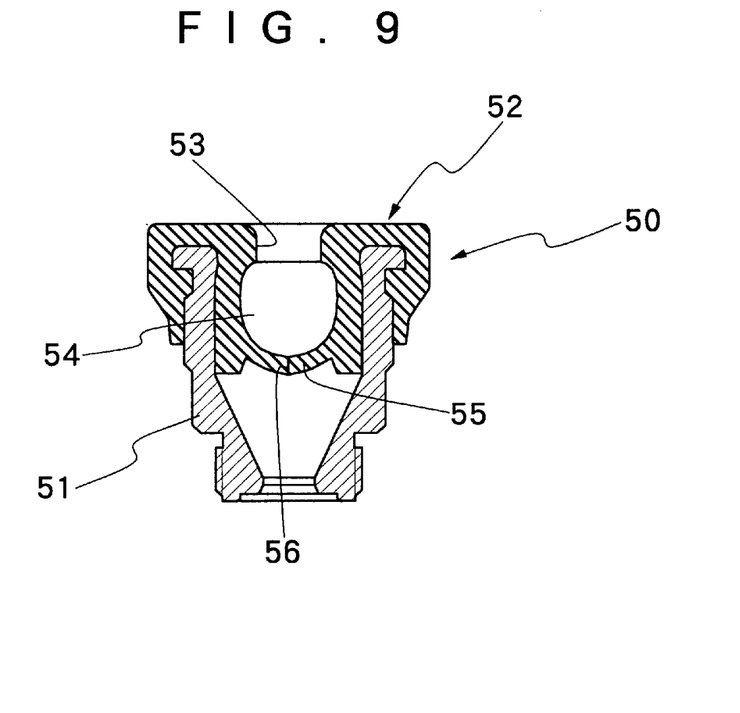
FIG. 9 is a schematic sectional view of a plug device according to a third embodiment of the present invention.

Further, illustrated in FIG. 9 is a plug device 50 according to a third embodiment of the present invention, in which a valve portion is arranged to serve also as a second throttle portion. More specifically, in this case, an outer shell member 51 contains a valve member 52 which can function as a valve member and at the same time as a pressure relief member. The valve member 52 is formed of a resilient material and provided with a first throttle portion 52 in the entrance passage of treating instruments, the throttle portion 52 having an aperture of such a diameter as to just fit on the circumference of a thick treating instrument substantially without leaving a gap space therearound. Formed on the inner side of the first throttle portion 54 is a pressure relief chamber 54 with a relatively broad space, and further formed on the inner side of the pressure relief chamber 54 is a thin concave wall portion 55 with a slit 56 which plays a dual as a valve and a second throttle portion.

With the arrangements just described, when no treating instrument is inserted in the entrance passage, the slit 56 is maintained in a closed state and atmospheric pressure prevails in the pressure relief chamber 54 by communication with the atmosphere through the aperture of the first throttle portion 54 which has a large open area. The slit 56 stays in a closed state and can maintain a seal in a secure manner even when the instrument channel is under vacuum pressure for endoscopic syphondrainage or under increased pressure to send compressed air into a body cavity. Nevertheless, for the purpose of enhancing hermetical tightness of the slit 56, it is desirable for the valve member 52 to have a girth slightly larger than the inside diameter of the outer shell member 51 and mounted in the latter through press-fitting, thereby constantly imposing a resilient force to the thin concave wall portion 55 to tighten the hermetical seal at the slit 56. By so doing, the slit 56 can be sealed to a sufficient degree although it is formed in the thinned-down concave wall portion 55.

On the other hand, upon inserting a treating instrument, more specifically, upon inserting a treating instrument of small diameter, only a minimum gap space is opened because the slit 56 is not spread largely on insertion of the instrument. Accordingly, at the time of insertion of a thin treating instrument, no pressure relieving function is required of the plug member in particular in preventing pressure discharges from the instrument channel 14, because contaminant body fluids in the instrument channel 14, if any, would not flow out through the slit 56. Especially, by press-fitting of the valve member 52 in the outer shell member 51, a resilient force constantly acts thereon to hold the slit 56 into a closed state, minimizing gap spaces around the inserted instrument.

Upon inserting a treating instrument of large diameter, the slit 56 is spread more widely to open a larger gap space around the circumference of the inserted instrument, but the passage is still in a constricted state. While the thick treating instrument is inserted further, the passage of communication between the pressure relief chamber 54 and the atmosphere is minimized to an extreme degree because the aperture diameter of the first throttle portion 53 has little difference from the outside diameter of the thick treating instrument. Therefore, the passage through the pressure relief chamber 54 is constricted more on the outlet or outer side rather than the inlet or inner side thereof, and, as a result, a pressure difference occurs between the instrument channel 14 and the pressure relief chamber 54 and also between the pressure relief chamber 54 and the atmosphere. At this time, since the pressure relief chamber 54 has a smaller pressure difference from the instrument channel 14 than from the atmosphere, contaminant body fluids within the instrument channel 14 of the endoscope, if any, are prevented from flowing out through the entrance passage of the instrument channel.

Figure 10:
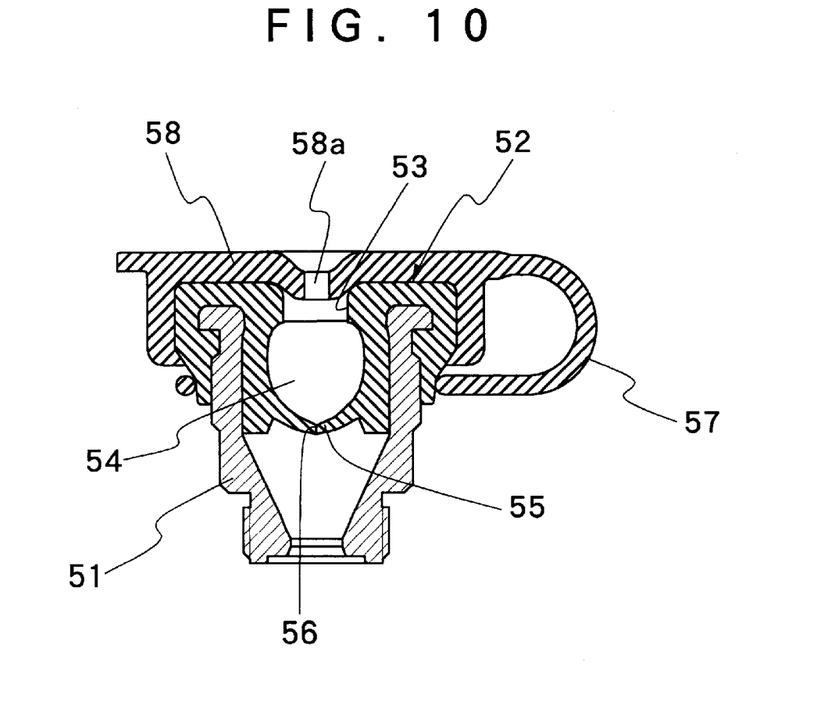
FIG. 10 is a schematic sectional view of the plug device of FIG. 9, which is fitted with a perforated lid member with a throttle aperture.

Alternatively, a resilient lid member 58 may be connected as shown in FIG. 10 by means of a connecting member 57. The resilient lid member 58 is provided with an aperture 58a of a diameter substantially corresponding to the outside diameter of a narrow treating instrument to serve as a first throttle member when a narrow instrument is inserted. Prior to insertion of a narrow treating instrument, the resilient lid member 58 is fitted in the valve member 52 to produce pressure relieving effects by the pressure relief chamber 54, in cooperation with the throttle portions which are formed by the aperture 58a and slit 56 on the outer and inner sides of the pressure relief chamber 54. When the resilient lid member 58 is removed from the valve member 52, a treating instrument of large diameter can be inserted into the plug device.

Figure 11:
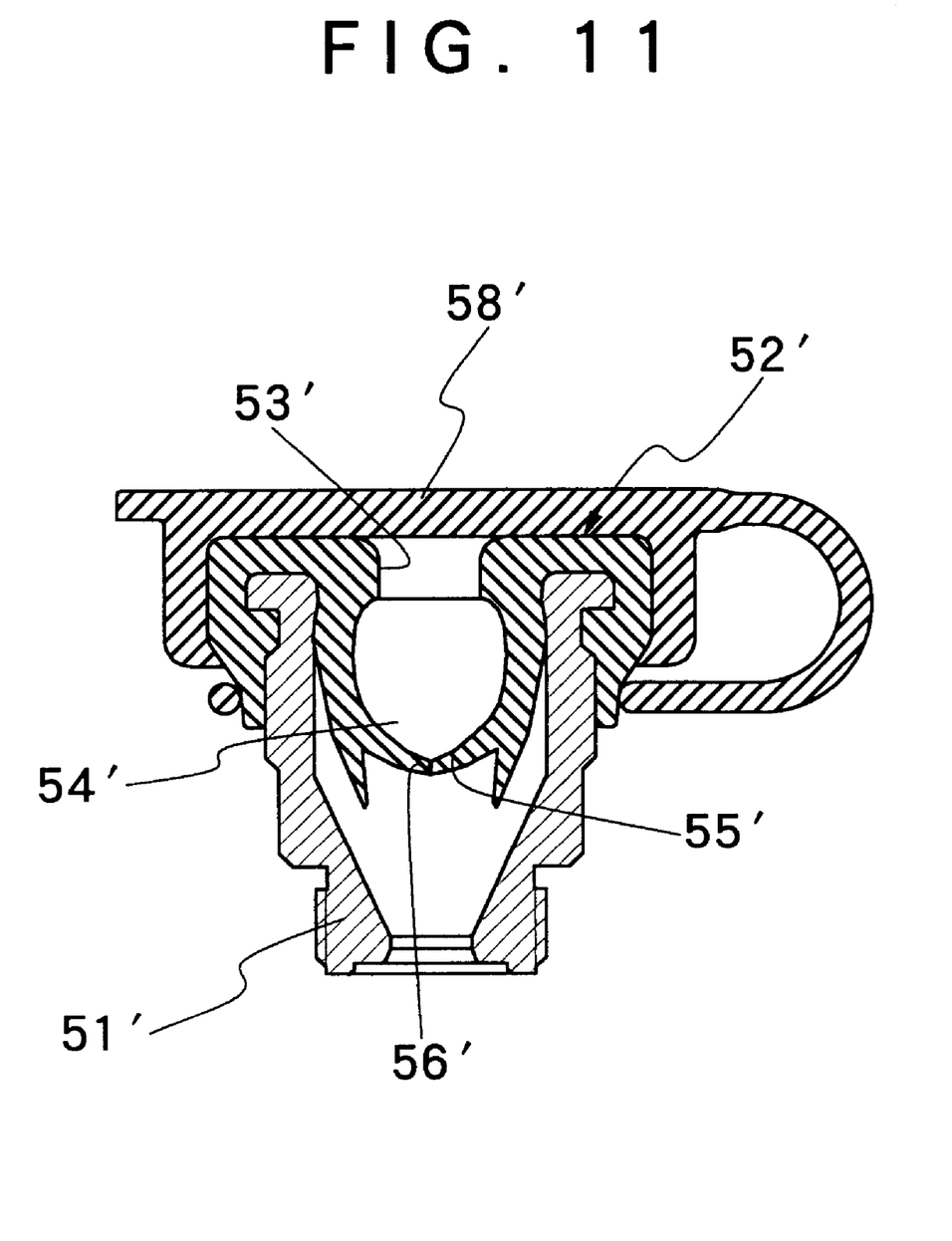
FIG. 11 is a schematic sectional view of a plug device, which is fitted with a blind lid member.

Further, as shown in FIG. 11, a blind lid 58' of resilient material may be fitted on a valve member 52'. In this case, when no treating instrument is inserted, the blind lid 58' is put on the valve member 52' to close a large aperture in a first throttle portion 53'. The lid member 58' contributes to enhance hermetical tightness of the valve member when a treating instrument is not used on the endoscope. Namely, the lid member 58' is removed prior to insertion of a treating instrument. In this case, the slit 56' in the valve member 52', which forms a pressure reduction mechanism in cooperation with first throttle portion 52' and pressure relief chamber 54', is not required to form a hermetical seal at the time of endoscopic syphondrainage, and there is no need for constantly applying resilient force to the thin concavely recessed wall portion 55' in a direction of closing the slit 56'. Therefore, in order to guarantee easy passage of treating instruments, lower portions of the valve member 52' may be disposed in a free state within the outer shell member 51, if desired, spaced apart from the inner periphery of the latter.

What is claimed is:

1. A plug device for endoscopic instrument channel, comprising:

an outer shell member to be fitted in an entrance passage to an endoscopic instrument channel;

a valve member formed of a resilient material and removably fitted in said shell member; and an instrument insertion passaged provided in and through said valve member and which is normally closed unless a treating instrument is inserted therein;

said instrument insertion passage including;

a slit wall portion located in an outermost portion of said instrument insertion passage, said slit wall portion being normally closed but being opened upon insertion of said treating instrument, an auxiliary pressure relief chamber provided on the inner side of said slit wall portion, a first throttle portion formed on the inner side of said first pressure relief chamber and having an open aperture area of a predetermined diameter, a main pressure relief chamber provided on the inner side of said first throttle portion, a main throttle portion provided on the inner side of said second pressure relief chamber, and including a flexible membrane having a smaller open aperture area than said first throttle portion, and said auxiliary pressure relief chamber forming an extended chamber of said main pressure relief chamber when a treating instrument having a predetermined diameter is inserted therein.

2. A plug device as defined in claim 1, wherein said flexible membrane has an inwardly converging shape.

3. A plug device as defined in claim 1, wherein said first and second throttle portions and said main pressure relief chamber are formed on a pressure relief member adapted to be fitted in said outer shell member, said valve member being adapted to be fitted in said outer shell member through said pressure relief member, and said auxiliary pressure relief chamber being formed between said pressure relief member and said valve member.

\* \* \* \* \*